United States Patent [19]

Schwarz et al.

[11] 4,404,131

[45] Sep. 13, 1983

[54] METHOD OF PRODUCING A FACTOR-VIII(AHF)-HIGH-CONCENTRATE

[75] Inventors: Otto Schwarz; Yendra Linnau, both of Vienna, Austria

[73] Assignee: Immuno Aktiengesellschaft für chemisch-medizinische Produkte, Vienna, Austria

[21] Appl. No.: 287,912

[22] Filed: Jul. 29, 1981

[30] Foreign Application Priority Data

Aug. 27, 1980 [AT] Austria .................................. 4338/80

[51] Int. Cl.³ .............................................. C07G 7/00
[52] U.S. Cl. ................................ 260/112 B; 424/101; 424/177
[58] Field of Search .................... 260/112 B; 424/101, 424/177

[56] References Cited

U.S. PATENT DOCUMENTS

| | | | |
|---|---|---|---|
| 3,631,018 | 12/1971 | Shanbrom et al. | 260/112 R |
| 3,652,530 | 3/1972 | Johnson et al. | 260/112 B |
| 3,682,881 | 8/1972 | Fekete et al. | 260/112 B |
| 3,869,436 | 4/1975 | Falksveden | 260/112 B |
| 4,069,216 | 1/1978 | Shanbrom | 260/112 B |
| 4,188,318 | 2/1980 | Shanbrom | 424/101 |

FOREIGN PATENT DOCUMENTS 349639 4/1979 Austria .
2624373 12/1977 Fed. Rep. of Germany .

OTHER PUBLICATIONS

Chem. Abst. 76:22762w.
Johnson, A., *Vox Sang* 36(2) 1979, pp. 72-76-Abst.
The New England Journal of Medicine 273, pp. 1443-1446 (1965).
J. Amer. Chem. Soc. 68, 459 (1946).
Arkiv för Kemi, 12, pp. 387-396 (1958).
Simonetti, et al., Hemostase 1, 57, (1961).
Proc. 11th Congr. Int. Soc. Blood Transf., No. 29, Part 4, p. 1109 (1966).

Primary Examiner—John C. Bleutge
Assistant Examiner—Patricia Short
Attorney, Agent, or Firm—Brumbaugh, Graves, Donohue & Raymond

[57] ABSTRACT

In a method of producing a factor-VIII(AHF)-high-concentrate having a specific activity of at least 2.5 units AHF and a fibrinogen content of less than 0.25 mg/mg protein from human or animal plasma, the plasma is subjected to a multi-step fractionation. The fraction purified by these fractionation measures and enriched in factor VIII (AHF) is subjected to a cryoalcohol precipitation and the resulting precipitate is processed into a stable form.

8 Claims, No Drawings

METHOD OF PRODUCING A FACTOR-VIII(AHF)-HIGH-CONCENTRATE

The invention relates to a method of producing a factor-VIII(AHF)-high-concentrate having a specific activity of at least 2.5 units AHF and a fibrinogen content of less than 0.25 mg/mg protein from human or animal plasma by a multi-step fractionation of the plasma, in particular by cryoprecipitation and purification by means of protein precipitating agents, such as polyethylene glycol.

Factor-VIII(AHF)-concentrates produced from human or animal plasma and exhibiting an increased factor-VIII-activity as compared to native plasma are already known. Known methods of producing factor-VIII-concentrates, as fractionation measures, employ a treatment of the plasma with ethanol, ether, polyethylene glycol and/or glycine. Also known is the cryoprecipitation of plasma according to Pool (1965, "The New England Journal of Medicine" 273, 1443) or the cryoethanol precipitation of plasma according to Johnson (Congr. Int. Soc. Blood Transf., Sydney, Australia, Abstracts of Paper, p. 1109 (1966)).

There are also other methods of producing factor-VIII-concentrates, i.e. the treatment of the plasma with adsorption agents, such as florigel, bentonit, ion exchangers, and permeation-chromatographic methods.

As far as the prior art concerns the treatment of plasma with ethanol, this was described for the first time by Cohn (J. Amer. Chem. Soc. 68, 459 (1946)). When treating the plasma with ethanol, the socalled Cohn-fraction I is obtained, which, however, possesses only a relatively low factor-VIII-activity. The Cohn-method was improved by Blombäck (Arkiv für Kemi, 12 387 (1958)), the Cohn-fraction I being further purified by extraction with an ethanol-glycine-citrate buffer. Therein the so-called fraction I-O was formed. As described by Simonetti et al. (Hemostase 1, 57 (1961)), the latter may be further purified with tannic acid; even these improved concentrates have only a relatively low factor-VIII-activity. These concentrates have also the disadvantage of possessing high contents of foreign proteins, i.e. factor-VIII-inactive protein contents. Thus, in the Cohn-fraction I more than 60% of the protein fibrinogen and in the Blombäck-fraction I-O even more than 80% of fibrinogen are contained.

Concerning the known fractionation by cryoprecipitation, this was carried out by deepfreezing and thawing human or animal plasma. The cryoprecipitate was dissolved in a buffer solution and, if desired, further purified by protein precipitation agents, such as polyethylene glycol and glycine. By the cryoprecipitation one has not succeeded in substantially increasing the factor-VIII-activity. The factor-VIII-activity, as compared to the starting plasma, is increased only by about 10 times, but also the further measures applied in combination with cryoprecipitation so far have not been successful in increasing the activity of the products obtained to the desired extent.

Multi-step fractionation methods in connection with a first cryoprecipitation step are described in U.S. Pat. Nos. 3,652,530, 3,631,018, 3,682,881 as well as in Austrian patent No. 349,639.

Such products are referred to as "highly purified AHF" or "High Purity AHF." Their factor-VIII-activity, however, also is only 90 to 100 times higher than that of native plasma, while the content of factor-VIII-inactive proteins (fibrinogen) still amounts to 35% of the total protein.

The invention aims at avoiding the disadvantages and difficulties pointed out and has as its object to provide a factor VIII-high-concentrate in which the inert, non-factor-VIII-active proteins are largely removed, the content of fibrinogen is kept as low as possible, and the factor-VIII-activity, based on the protein present in the concentrate, is higher than with known therapeutically used preparations. In particular, it is an object of the invention to provide a method of producing a factor-VIII(AHF)-high-concentrate with a specific activity of at least 2.5 units AHF and a fibrinogen content of less than 0.25 mg/mg protein, which method is applicable on an industrial and technical scale, ensuring a high economy.

Using a multi-step fractionation process as described in the beginning, in which a cryoprecipitation is performed preferably as a first step, the aforesaid object is achieved in that a fraction purified by these fractionation measures and enriched in factor VIII (AHF) is subjected to a cryoalcohol precipitation and the resulting precipitate is processed into a stable form.

According to a preferred embodiment of the invention a mono or polyvalent alcohol, such as methyl alcohol, ethyl alcohol, polyethylene glycol or polyester glycol (PLURONIC®) is added to the purified and factor-VIII(AHF)-enriched fraction at a pH of 5.9 to 6.3 and a temperature of from 0° to −3° C., the mixture is deepfrozen and then thawed at a temperature of from 0° to 4° C., whereupon the precipitate containing the AHF-high-concentrate is dissolved and processed into a stable form by deepfreezing and lyophilization.

A preferred embodiment of the invention comprises the combination of the following measures:

that human or animal plasma is subjected to a first cryoprecipitation;

that the cryoprecipitate is dissolved in an aqueous buffer solution, adjusted to a pH of from 6.15 to 6.25 and the solution is subjected to a first purification precipitation with polyethylene glycol;

that the supernatant obtained after discarding the precipitate is subjected to at least one further purification precipitation with polyethylene glycol; and that the purified and factor-VIII(AHF)-enriched fraction finally obtained after discarding the precipitates is subjected to the cryoalcohol precipitation by adding to this fraction a mono or polyvalent alcohol, such as methyl alcohol, ethyl alcohol, polyethylene glycol or polyester glycol (PLURONIC®), the mixture is deepfrozen and then thawed at a temperature of from 0° to 4° C., whereupon the precipitate containing the AHF-high-concentrate is dissolved and processed into a stable form by deepfreezing and lyophilization.

Advantageously, the first polyethylene glycol precipitation is carried out with 3 w/v % polyethylene glycol and the second and further polyethylene glycol precipitations are carried out with 8 w/v % polyethylene glycol.

Suitably, an about 10 w/v % PLURONIC® solution is used for precipitating the factor-VIII-concentrate.

Instead of polyethylene glycol as a protein precipitating agent, PLURONIC® may also be used, in which case the combination consists in the following characteristic features:

that human or animal plasma is subjected to a first cryoprecipitation;

that the cryoprecipitate is dissolved in an aqueous buffer solution, adjusted to a pH of 6.25 and the solution is subjected to a first purification precipitation with PLURONIC ®;

that the supernatant obtained after discarding the precipitate is subjected to at least one further purification precipitation with PLURONIC ®; and that the purified and factor-VIII(AHF)-enriched fraction finally obtained after discarding the precipitates is subjected to the cryoalcohol precipitation by adding a mono or polyvalent alcohol, such as methyl alcohol, ethyl alcohol, polyethylene glycol or polyester glycol (PLURONIC ®) to this fraction; the mixture is deepfrozen and then thawed at a temperature of from 0° to 4° C., whereupon the precipitate containing the AHF-high-concentrate is dissolved and brought into a preservable form by deepfreezing and lyophilization.

The method according to the invention will now be explained in more detail by way of the following examples:

EXAMPLE 1

460 l fresh frozen plasma are thawed at 0° and +4° C. The cryoprecipitate formed is separated by centrifugation and dissolved in 9.6 l trisodiumcitrate at 37° C.

The pH of the solution is adjusted to 6.2 and 3 w/v % polyethylene glycol 2000 is added. A precipitate is forming, which is separated by centrifugation and discarded.

The ionic strength of the supernatant, which contains factor VIII (AHF), is increased by the addition of trisodiumcitrate. The remaining undesired proteins are precipitated by increasing the polyethylene glycol 2000 concentration to 8 w/v % and are discarded after centrifugation.

By the addition of 8 w/v % ethanol at −2° C. and a pH of 6.1 the factor-VIII-concentrate is precipitated; the suspension is deepfrozen and after thawing at +4° C. the factor-VIII-containing cryoalcohol precipitate is dissolved in a physiologic buffer, sterile filtered, filled into final containers and lyophilized.

EXAMPLE 2

9,600 ml fresh frozen plasma are thawed at 0° to +4° C. The centrifuged cryoprecipitate is dissolved in 240 ml trisodiumcitrate at 37° C.

The pH of the solution is adjusted to 6.2 and 3 w/v % polyethylene glycol 2000 are added. The resulting precipitate is separated and discarded.

By the addition of trisodiumcitrate the ionic strength is increased, by the addition of further polyethylene glycol 2000 up to a concentration of 8 w/v % undesired proteins are precipitated; these are separated and discarded.

At a pH of 6.0 and a temperature of −2° to −3° C. factor-VIII-concentrate is precipitated by means of 10 w/v % methanol; the suspension is frozen and, after thawing, the cryoalcohol precipitate is dissolved in an isotonic buffer, sterile filtered, filled into final containers and lyophilized.

EXAMPLE 3

The procedure of Example 2 is repeated, however, with a concentration of 12 w/v % polyethylene glycol being used for precipitating the factor-VIII-concentrate, instead of 10 w/v % methanol.

EXAMPLE 4

The procedure of Example 2 is repeated, however, with a concentration of 10 w/v % PLURONIC ® being used for precipitating the factor-VIII-concentrate, instead of 10 w/v % methanol.

EXAMPLE 5

10.4 l fresh frozen plasma are thawed at 0° to +4° C. The cryoprecipitate is dissolved in 250 ml trisodiumcitrate buffer.

The pH of the solution is adjusted to 6.3 and 2.5 w/v % PLURONIC ® is added. The precipitate is discarded. After increasing the ionic strength, the PLURONIC ® concentration is increased to 7.5 w/v % and the precipitate is discarded once more.

The supernatant is treated with 8 w/v % ethanol, at a pH of 6.0 and a temperature of −2° C., factor-VIII-concentrate thus precipitating. The suspension is frozen and, after thawing at +4° C., the cryoalcohol precipitate is separated.

The specific activity of the high concentrates obtained, which has been substantially increased by the method according to the invention, and the AHF enrichment by more than 200 times relative to the starting plasma is illustrated in Table I in comparison to known commercially available AHF-concentrates.

TABLE I

|  | Specificity unit/mg | Purity as compared to plasma |
|---|---|---|
| Plasma | 0.017 | 1 |
| Cryoprecipitate | 0.145 | 9 times |
| High Purity AHF | 1.667 | 98 times |
| High concentrate, produced according to invention | >3.500 | 206 times |

The lower content of fibrinogen of the high concentrate according to the invention as compared to known concentrates may be derived from Table II.

TABLE II

| Cohn-fraction I | ≧60% fibrinogen |
|---|---|
| Blomback-fraction I-O | ≧80% fibrinogen |
| Purified or High Purity AHF | ≧35% fibrinogen |
| High concentrate produced according to invention | 10% fibrinogen |

What we claim is:

1. An improved method of producing a factor-VIII(AHF)-high-concentrate having a specific activity of at least 2.5 units AHF and a fibrinogen content of less than 0.25 mg/mg protein from human or animal plasma by a multi-step fractionation of said plasma, in particular by cryoprecipitation and purification by means of protein precipitating agents, such as polyethylene glycol, wherein the improvement comprises subjecting a solution fraction purified by these multi-step fractionation measures and enriched in factor VIII(AHF) to a deepfreezing and thawing operation in the presence of an alcohol and processing the resulting precipitate into a stable form.

2. A method as set forth in claim 1, wherein to the purified and factor-VIII-enriched fraction, a mono or polyvalent alcohol selected from the group consisting of methyl alcohol, ethyl alcohol, polyethylene glycol and polyester glycol (PLURONIC ®) is added at a pH of from 5.9 to 6.3 and a temperature of from 0° to −3°

C. so as to obtain a mixture, said mixture is deepfrozen and then thawed at 0° to 4° C. with a precipitate containing AHF-high-concentrate forming, and said precipitate is dissolved and processed into a stable form by deepfreezing and lyophilization.

3. A method as set forth in claim 1, characterized by a combination of the following measures:

subjecting human or animal plasma to a first cryoprecipitation so as to obtain a cryoprecipitate, dissolving said cryoprecipitate in an aqueous buffer solution so as to obtain a solution, said solution being adjusted to a pH of from 6.15 to 6.25 and subjected to a first purification precipitation with polyethylene glycol so as to obtain a precipitate, discarding said precipitate so as to obtain a supernatant, said supernatant being subjected to at least one further purification precipitation with polyethylene glycol so as to obtain at least one further precipitate, discarding said at least one further precipitate so as to obtain a purified and factor-VIII(AHF)-enriched fraction, said purified and factor-VIII(AHF)-enriched fraction being subjected to a cryoalcohol precipitation by adding to this fraction a mono or polyvalent alcohol selected from the group consisting of methyl alcohol, ethyl alcohol, polyethylene glycol and polyester glycol (PLURONIC ®) so as to obtain a mixture, deepfreezing said mixture and then thawing said mixture at 0° to 4° C. with an AHF-high-concentrate-containing precipitate forming, said AHF-high-concentrate-containing precipitate being dissolved and processed into a stable form by deepfreezing and lyophilization.

4. A method as set forth in claim 3, wherein the first polyethylene glycol precipitation is carried out with 3 w/v % polyethylene glycol and the at least one further polyethylene glycol precipitation is carried out with 8 w/v % polyethylene glycol.

5. A method as set forth in claim 4, wherein an approximate 10 w/v % PLURONIC ® solution is used for precipitating said factor-VIII(AHF)-high-concentrate.

6. A method as set forth in claim 1, characterized by the combination of the following measures:

subjecting human or animal plasma to a first cryoprecipitation so as to obtain a cryoprecipitate, dissolving said cryoprecipitate in an aqueous buffer solution so as to obtain a solution, said solution being adjusted to a pH of 6.25 and subjected to a first purification precipitation with PLURONIC ® so as to obtain a precipitate, discarding said precipitate so as to obtain a supernatant, said supernatant being subjected to at least one further purification precipitation with PLURONIC ® so as to obtain at least one further precipitate, discarding said at least one further precipitate so as to obtain a purified and factor-VIII(AHF)-enriched fraction, said purified and factor-VIII(AHF)-enriched fraction being subjected to a cryoalcohol precipitation by adding to this fraction a mono or polyvalent alcohol selected from the group consisting of methyl alcohol, ethyl alcohol, polyethylene glycol and polyester glycol (PLURONIC ®) so as to obtain a mixture, deepfreezing said mixture and then thawing said mixture at 0° to 4° C. with an AHF-high-concentrate-containing precipitate forming, said AHF-high-concentrate-containing precipitate being dissolved and processed into a stable form by deepfreezing and lyophilization.

7. An improved factor-VIII(AHF)-high-concentrate having a specific activity of at least 2.5 units AHF and a fibrinogen content of less than 0.25 mg/mg protein prepared from human or animal plasma by a multi-step fractionation of said plasma, in particular by cryoprecipitation and purification by means of protein precipitating agents, such a polyethylene glycol, wherein the improvement comprises subjecting a solution fraction purified by these multi-step fractionation measures and enriched in factor VIII(AHF) to a deepfreezing and thawing operation in the presence of an alcohol and processing the resulting precipitate into a stable form.

8. An improved factor-VIII(AHF)-high-concentrate having a specific activity of at least 2.5 units AHF and a fibrinogen content of less than 0.25 mg/mg protein prepared according to the method described in claim 2, 3, 4 or 5.

* * * * *